US005674854A

United States Patent [19]
Bodley et al.

[11] Patent Number: 5,674,854
[45] Date of Patent: Oct. 7, 1997

[54] INCLUSION COMPLEX OF BETA-CYCLODEXTRIN AND DICLOFENAC, ITS PREPARATION AND USE

[75] Inventors: Mark David Bodley, Port Elizabeth; Mino Rodolfo Caira, Cape Town; Lueta Ann Glintenkamp, Port Elizabeth; Vivienne Jean Griffith; Luigi Renzo Nassimbeni, both of Cape Town; Douglas George Murray Nicholson; Lawrence John Penkler, both of Port Elizabeth; Michiel Coenraad Bosch Van Oudtshoorn, Pretoria, all of South Africa

[73] Assignee: Farmarc Nederland BV, Amsterdam, Netherlands

[21] Appl. No.: 319,548

[22] Filed: Oct. 7, 1994

[30] Foreign Application Priority Data

Oct. 8, 1993 [ZA] South Africa ............... 93/7480

[51] Int. Cl.$^6$ .................. A61K 31/715; A61K 9/50
[52] U.S. Cl. .................. 514/58; 514/964; 424/499
[58] Field of Search .................. 514/54, 58, 825, 514/886, 916, 964; 536/103, 123.1; 424/499

[56] References Cited

U.S. PATENT DOCUMENTS 5,324,750  6/1994  Lincoln et al. .................. 514/570

FOREIGN PATENT DOCUMENTS

| 0519428 | 12/1992 | European Pat. Off. . |
| 42007922 | 9/1993 | Germany . |
| 0848156 | 10/1984 | South Africa . |
| 0912282 | 3/1991 | South Africa . |
| 90002141 | 3/1990 | WIPO . |
| 9200725 | 1/1992 | WIPO . |

OTHER PUBLICATIONS

Song et al. *Yanbian Yixueyuan Xuebae*, vol. 16(4), pp. 269–273, (1993). [Abstract Only].
*Biophysical Chemistry Part II*, Ed. Cantor & Schimmel, pp. 756–757, Publ. W. H. Freeman and Co., (1980).
T. Backensfeld et al., "Solubilization of Non–Steroidal Antirheumatics with Cyclodextrins and Cyclodextrin Ethers", 1990, 323, p. 690.
T. Backensfeld et al., "Interaction of NSA with Cyclodextrins and Hydroxypropyl Cyclodextrin Derivatives" 1991, 74, pp. 85–93.
Orienti et al., "Inclusion Complexes between Non–Steroidal Antiinflammatory Drugs and β–Cyclodextrin", Eur. J. Pharm. Biopharm, 1991, 37, pp. 110–112.
Orienti, "Availability of Nsaidh β–Cyclodextrin Inclusion Complexes", 1989, 322, pp. 207–211 Arch. Pharm. (Weinheim).
Nekroshus, "Preparing the Inclusion Compounds Orthophen and Inodomethcin with β–Cyclodextrin and Their Derivatographic Analysis", 1989, 38, 39, pp. 259–261.
Devi, "Albumin Microspheres and Beta–Cyclodextrin Inclusion Complex Containing Diclofenac Sodium" Ind. J. Pharm. Sci. 1992, 54, pp. 259–261.
Kurozumi, "Inclusion Compounds of Non–Steroidal Antiinflammatory and Other Slightly Water Soluble Drugs with α–and β–Cyclodextrins In Powered Form", Chem. Pharm. Bull. 1975, 23, pp. 3062–3068.
English Abstract of Japanese Patent Application No. 60–16547 to Wakamoto Pharmaceutical Co., Ltd.
English Abstract of Japanese Patent Application No. 59–084821 to Teikoku Chemical Industries, Ltd.
M. Otagiri et al., "Comparataive Study on Inclusion Complexation of β–Cyclodextrin and Tri–O–Methyl–β–Cyclodextrin with Several Drugs In Aqueous Solution", ACTA Pharm. Suec. 21, 1984, pp. 357–366.
K. Ikeda et al., "Inclusion Complexes of β–Cyclodextrin with Antiinflammatory Drugs Fenamates In Aqueous Solution", Chem. Pharm. Bull. 23(1), 1975, pp. 201–208.
European Patent Office Abstracts of JP–A–6 016 547, Jan. 25, 1994 and vol. 18, No. 222, Apr. 21, 1994.
Database Chemabs, Chemical Abstracts Service, Columbus, Ohio, AN: 115:239451 (Abstract).
Database Chemabs, Chemical Abstracts Service, Columbus, Ohio, AN: 110:218958 (Abstract).

*Primary Examiner*—John Kight
*Assistant Examiner*—Howard C. Lee
*Attorney, Agent, or Firm*—Cushman Darby & Cushman Intellectual Property Group of Pillsbury Madison & Sutro LLP

[57] ABSTRACT

An inclusion complex of diclofenac, preferably as diclofenac sodium, and an unsubstituted beta-cyclodextrin has the formula 1 molecule of diclofenac to 1 molecule of the unsubstituted beta-cyclodextrin and preferably from 5 to 11 water molecules. The inclusion complex may be formulated as a pharmaceutical composition.

9 Claims, 7 Drawing Sheets

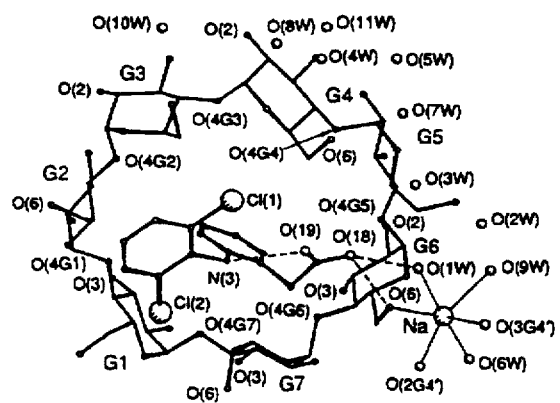
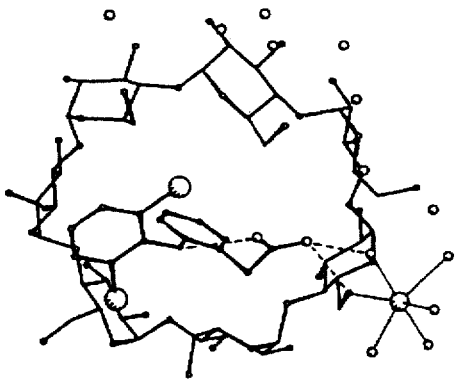
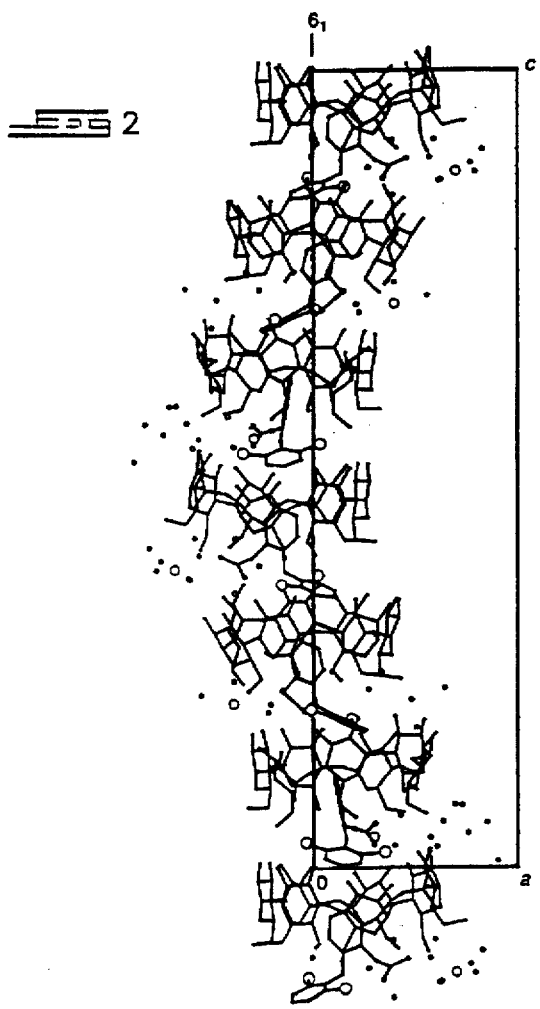

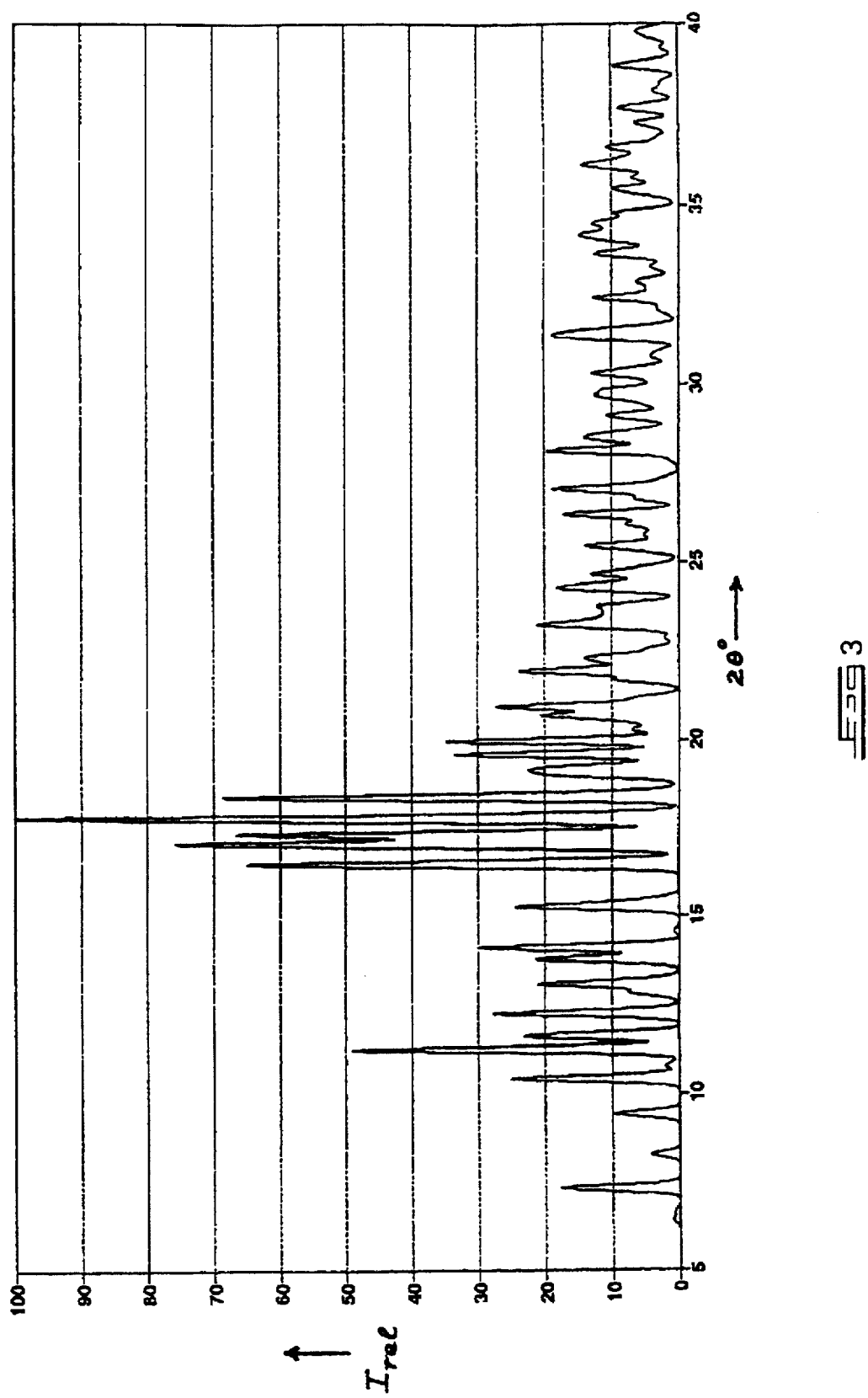

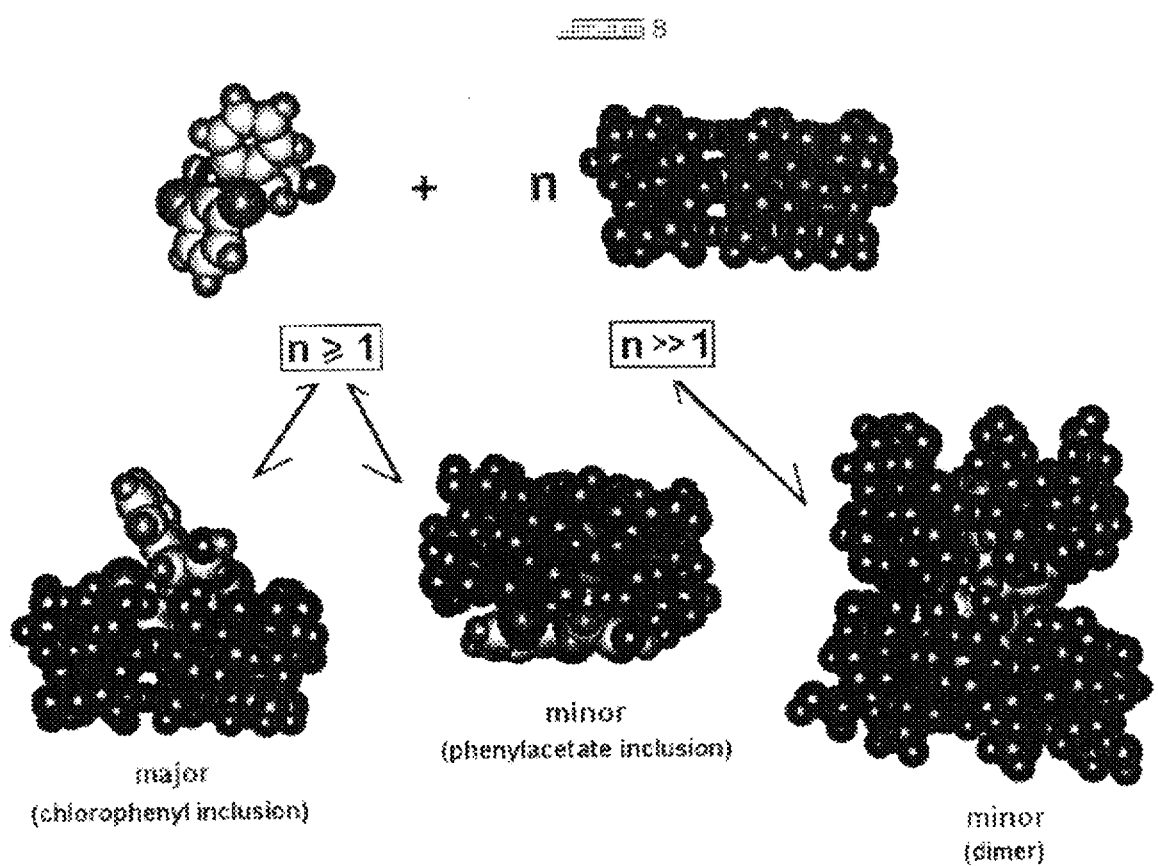

INCLUSION COMPLEX OF BETA-CYCLODEXTRIN AND DICLOFENAC, ITS PREPARATION AND USE

BACKGROUND OF THE INVENTION

This invention relates to an inclusion compound or complex of diclofenac or a pharmaceutically acceptable salt thereof and a β-cyclodextrin.

Diclofenac, also known as 2-[(2,6-dichlorophenyl)amino] benzeneacetic acid or ([o-2,6-dichloroanilino)phenyl] acetic acid, and its salts are well known anti-inflammatory agents.

β-cyclodextrin is a cyclic compound consisting of seven units of α-(1→4) linked D-gluco-pyranose units, and is used as a complexing agent.

The properties of cyclodextrins and numerous inclusion complexes are well known and have been reviewed in detail [see Szejtli, J. Cyclodextrin Technology (1988) Kluwer Academic Publishers, Dordrecht]. Briefly, cyclodextrins are commercially available cyclic oligosaccharides composed of 6, 7 or 8 glucopyranose units (alpha-, beta- and gamma-cyclodextrin respectively) characterized by a cone-like molecular shape. The cavity of the cone is hydrophobic whilst the exterior is hydrophilic. The hydrophobic nature of the cavity endows the molecule with the ability to form inclusion complexes with hydrophobic guest molecules of suitable size to fit into the cavity of the host. The inclusion complex may be stabilized by a number of forces including van der Waals attractive forces and hydrogen bonding. Polar (ionized) groups are less readily included than less-polar (unionized) groups.

Cyclodextrin inclusion complexes may be prepared on the basis of liquid state, solid state or semi-solid state reaction between the components. The former is accomplished by dissolving the cyclodextrin and guest in a suitable solvent or mixture of solvents and subsequently isolating the solid state complex by crystallization, evaporation, spray drying or freeze drying. In the solid state method, the two components may be screened to uniform particle size and thoroughly mixed whereafter they are ground in a high energy mill with optional heating, screened and homogenized. In the semi-solid state, the two components are kneaded in the presence of small mounts of a suitable solvent, and the complex so-formed, is oven dried, screened and homogenized. The liquid state reaction generally provides optimum conditions for completeness of reaction.

Cyclodextrin inclusion complexation of a suitable guest results in a number of physicochemical changes in the properties of the guest. Firstly, the melting characteristics of the guest are absent in the cyclodextrin inclusion complex, which generally begins to decompose without melting between 250°–300° C. Secondly, the infrared spectrum and X-ray powder diffraction pattern of the complex are distinct relative to the pure guest or simple (non-complexed) mixtures of host and guest. Thirdly, a water insoluble guest may be rendered water soluble by cyclodextrin inclusion complexation. In many cases chemically unstable guests are stabilized by inclusion complexation. The foregoing changes in the physicochemical properties of the guest on inclusion complexation with a cyclodextrin provide evidence that the cyclodextrin inclusion complex represents an unique solid state form of the guest molecule.

Depending on solvent conditions, the dissolved inclusion complex exists in equilibrium between uncomplexed host and guest and complexed host/guest. Orally administered cyclodextrin-drug inclusion complexes generally result in rapid absorption of the drug, facilitated by the cyclodextrin, whereas the cyclodextrin is not absorbed to any significant extent. Additionally cyclodextrin inclusion complexes of certain drugs have been shown to reduce gastrointestinal side effects [see Fromming, K.-H. & Szejtli, J. Cyclodextrins in Pharmacy (1988), Kluwer Academic Publishers]. Cyclodextrins therefore possess ideal properties as true drug carriers. Cyclodextrins and their inclusion complexes possess favourable flow, binding and compaction properties facilitating tablet compression.

Microencapsulation of drug molecules in cyclodextrins (CDs) has been extensively used in the pharmaceutical industry to produce more stable drug preparations with improved bioavailability. With a view to predicting crystal packing arrangements in CD complexes, systematic analyses of available crystallographic data have been undertaken and several general conclusions have been drawn regarding their overall packing tendencies.

The following relevant prior art is known in relation to inclusion complexes of cyclodextrins and diclofenac.

(1) Beta-cyclodextrin and particularly hydroxyalkyl ether derivatives have been reported to increase the aqueous solubility of diclofenac [Solubilization and Stabilization of Non-Steroidal Antirheumatics with Cyclodextrins and Cyclodextrin Ethers, Backensfeld, T. and Mueller, B. W. Arch. Pharm. 1990, 323, 690; Interaction of NSA with cyclodextrins and hydroxypropyl cyclodextrin derivatives, Backensfeld, T.; Mueller, B. W. and Kolter, K. Int. J. Pharm. 1991, 74, 85–93].

(2) The interaction of diclofenac with beta-cyclodextrin as a function of temperature and pH has been reported [Inclusion Complexes between Non Steroidal Antiinflammatory Drugs and β-Cyclodextrin, Orienti, I., Fini, A., Bertasi, V. and Zecchi, V. Eur. J. Pharm. Biopharm. 1991, 37, 110–1121.

The above studies (1 and 2) rely on phase solubility analysis which involves the determination of the effect of increasing concentrations of cyclodextrin on the solubility of excess diclofenac sodium under a variety of conditions. Them is no mention of the preparation or isolation of a solid inclusion complex.

(3) The diffusability of a diclofenac (acid) complex with beta cyclodextrin has been reported [Availability of NSAIDH β-Cyclodextrin Inclusion Complexes, Orienti, I., Cavallari, C. and Zecchi, V. Arch. Pharm (Weinheim) 1989, 322, 207–211]. The complex was prepared according to a previously described coprecipitation method involving addition of the drug, dissolved in ethyl ether, to a solution of cyclodextrin in water, agitating for 24 hours, cooling, isolating product, washing with ethyl ether and drying. The complex was not characterized and stoichiometry was only assumed to be 1:1.

(4) An inclusion complex of diclofenac sodium and beta-cyclodextrin has been prepared by concurrent crystallization from water-organic systems. [Preparing the inclusion compounds orthophen and indomethacin with beta-cyclodextrin and their derivatographic analysis, Nekroshus, E. S. and Reshetnyak, V. Y. Farmatsiya Moscow 1989, 38, 29–34]. The findings of derivatographic analysis and thin layer chromatography provide support of drug-cyclodextrin inclusion at a molar ratio of 1:2.

(5) An inclusion complex of diclofenac sodium and beta cyclodextrin was formulated as microspheres using crosslinked egg albumin and hydroxypropylmethylcellose [Albumin Microspheres and Beta-cyclodextrin Inclusion Complex Containing Diclofenac Sodium, Devi, S. G et al. Ind. J. Pharm. Sci. 1992, 54, 259–261]. Relative to free diclofenac sodium poor overall release was obtained for the complex as measured by diffusion of the drug across dialysis membrane. Details of preparation of the complex are not described and neither are any analytical methods described to provide evidence of complexation.

In the above studies (3 and 4) the so-called co-precipitation method of complex formation is described. The co-precipitation method is known generally to produce low yields of complex [Inclusion Compounds of Non-Steroidal Antiinflammatory and other slightly water soluble drugs with α- and β-Cyclodextrins in Powdered Form; Kurozumi, M. et al. Chem. Pharm. Bull. 1975,23, 3062–3068]. Additionally, the frequent use of ethyl ether (3 and 4) is undesirable in the industry owing to explosion and narcotic hazards. The tendency for inclusion of ethyl ether also presents potential risk of high residual ether levels in the dried complex rendering the product unsuitable for pharmaceutical application.

(7) PCT WO90/02141 to Australian Commercial Research and Development Limited teaches inclusion complexes comprising an amino cyclodextrin derivative wherein at least one C2,C3 or C6 hydroxyl is substituted with $NH_2$, and inclusion complexes comprising a cyclodextrin having at least one substitution where a C2, C3 or C6 hydroxyl is substituted with a group selected from a particular list, the active component of the complex being for example diclofenac. In addition this reference covers a pharmaceutical composition for oral administration containing such an inclusion complex. There is no specific disclosure of an inclusion complex of diclofenac or diclofenac sodium and an unsubstituted beta-cyclodextrin.

(8) European Patent Application No 519428 to Takeda Chemical Industries Limited teaches a pharmaceutical composition comprising a slightly water soluble drug, for example diclofenac, a cyclodextrin and a water soluble organic solvent, particularly for injection. It is mentioned that in many cases the composition forms an inclusion compound with the cyclodextrin. It is also mentioned that the cyclodextrin may be beta-cyclodextrin. There is no disclosure of an inclusion complex of diclofenac or diclofenac sodium and an unsubstituted beta-cyclodextrin.

(9) Japanese Patent Application No JP59084821 to Teikoku Chemical Industries Limited teaches a sustained release preparation of diclofenac which contains cyclodextrin. The molar ratio of cyclodextrin to diclofenac is 0.05–1.0. Alpha-cyclodextrin, beta-cyclodextrin or gamma-cyclodextrin may be used. In the preparation of this product, diclofenac is mixed with cyclodextrin. After the addition of water, the mixture is kneaded and dried. Alternatively, diclofenac and cyclodextrin are added to water and stirred well. After filtration, the filtrate is sprayed and dried or lyophilized. There is no indication of the formation of an inclusion complex.

(10) Japanese Patent Application No JP6016547 to Wakamoto Pharmaceutical Company Limited teaches an antiphlogistic eyedrop which comprises a diclofenac sodium salt and at least one water soluble cyclodextrin, being a substituted cyclodextrin. There is no indication that the diclofenac and the cyclodextrin form an inclusion complex.

(11) German Patent Application No 4207922 to Pharmatech GmbH teaches water soluble inclusion complexes of diclofenac sodium and either methyl-beta-cyclodextrin with a degree of substitution of 0.4, methyl-beta cyclodextrin with a degree of substitution of 0.6 or hydroxypropyl-beta cyclodextrin with a degree of substitution of 0.42. There is no teaching of an inclusion complex of diclofenac or diclofenac sodium and an unsubstituted beta-cyclodextrin. South African Patent No 84/8156 to Chiesi Farmaceutici SpA teaches compounds obtained by complexation of piroxicam with α-, β-, or γ-type cyclodextrins, in ratios comprising between 1:1 and 1:10 of piroxicam and cyclodextrin respectively. These compounds may be used in pharmaceutical compositions, particularly suitable for oral administration.

South African Patent No 91/2282 to Chiesi Farmaceutici SpA teaches a novel process for the production of piroxicam-cyclodextrin complexes wherein the piroxicam and the cyclodextrin, both in powder form, are mixed together in the solid state and optionally degassed, the mixture obtained is co-ground in a high energy mill with the grinding chamber saturated with steam, and the product obtained is dried under vacuum and screened to eliminate any aggregates.

There is a need for a novel inclusion complex of diclofenac and a cyclodextrin.

SUMMARY OF THE INVENTION

According to a first aspect of the invention there is provided an inclusion complex of diclofenac or a pharmaceutically acceptable salt thereof and an unsubstituted beta-cyclodextrin which has a molar ratio of diclofenac or a pharmaceutically acceptable salt thereof to the unsubstituted beta-cyclodextrin of 1:1.

The inclusion complex preferably includes water and has a molar ratio of diclofenac or a pharmaceutically acceptable salt thereof to the unsubstituted beta-cyclodextrin to water of about 1:1:5 to 1:1:11.

Preferably, the inclusion complex has a solubility in deionized water of greater than 10 mg of diclofenac or the pharmaceutically acceptable salt thereof per milliliter at 20° C.

Preferably, the diclofenac is present in the complex as diclofenac sodium.

According to a second aspect of the invention there is provided an inclusion complex of diclofenac sodium and an unsubstituted beta-cyclodextrin which has a molar ratio of diclofenac sodium to the unsubstituted beta-cyclodextrin of 1:1 and which has substantially the X-ray powder diffraction pattern of FIG. 3.

The representative X-ray powder diffraction pattern of FIG. 3 was generated from the unit cell data, space group data, fractional atomic co-ordinates and thermal parameters of the atoms determined from a single crystal X-ray structure analysis as described in Example 1. The pattern was calculated over the 2 theta range 6°–40° from Cu-Kα radiation (λ=1.5418 Å) using the program LAZY PULVERIX. (See Yvon, N.; Jeitschko, W.; and Parthé E. J. (1977) J. Appl. Crystallogr., 10, 73–74).

The inclusion complex of diclofenac sodium and the unsubstituted beta-cyclodextrin preferably has the formula

(diclofenac sodium).(beta-cyclodextrin).11 $H_2O$.

This inclusion complex preferably crystallizes in layers of plane group p6 parallel to the (001) plane, complex molecules in each successive layer being rotated by 60° about the c-axis from the complex molecules in the layer above.

More preferably, this complex has the structure substantially as illustrated in FIG. 1.

The diclofenac may also be present in the complex as diclofenac potassium.

According to a third aspect of the invention there is provided a process for preparing an inclusion complex of diclofenac or a pharmaceutically acceptable salt thereof and an unsubstituted beta-cyclodextrin which includes the steps of:

(a) mixing the diclofenac or the pharmaceutically acceptable salt thereof and the beta-cyclodextrin;

(b) adding a suitable amount of water to the mixture of step (a) with vigorous mixing until a paste or a slurry is formed;

(c) continuing the mixing with further addition of water if necessary to maintain the paste or the slurry consistency, for a suitable period of time to form the inclusion complex; and (d) drying the product of step (c).

Preferably, in step (c) the mixing is continued for a period of time from 0.25 hours.

According to a fourth aspect of the invention there is provided a process for preparing an inclusion complex of diclofenac or a pharmaceutically acceptable salt thereof and an unsubstituted beta-cyclodextrin which includes the steps of:

(e) dissolving a suitable amount of diclofenac or a pharmaceutically acceptable salt thereof and a suitable amount of an unsubstituted beta-cyclodextrin in water at an elevated temperature; and (f) cooling the solution and allowing the formation of the inclusion complex by evaporation of the water over a period of time.

The temperature in step (e) is preferably around 70° C.

The period of time for evaporation in step (f) is preferably from 1 hour.

According to a fifth aspect of the invention there is provided a pharmaceutical composition which comprises as the active ingredient an inclusion complex of diclofenac or a pharmaceutically acceptable salt thereof and an unsubstituted beta-cyclodextrin as defined above.

The pharmaceutical composition may be formulated for oral administration.

BRIEF DESCRIPTION OF THE DRAWINGS

FIG. 1 is a stereo drawing of a diclofenac sodium-β-cyclodextrin inclusion complex of the invention viewed from the primary β-CD face. H atoms are omitted. Three of the hydrogen bonds referred to in the specification are indicated by dashed lines;

FIG. 2 is a projection showing the helical arrangement in one stack of complex molecules according to the invention;

FIG. 3 is a representative X-ray powder diffraction pattern for the inclusion compound beta-cyclodextrin diclofenac sodium undecahydrate as described in Example 1;

FIG. 7A is a continuous variation plot for beta-cyclodextrin 3' and 5' protons with the chemical shift difference being relative to free beta-cyclodextrin ($\times 10^{-3}$ ppm) and with [BCD] being total beta-cyclodextrin concentration (mMol). FIG. 7B is a continuous variation plot for diclofenac B,E,F and H protons with chemical shift difference being relative to free diclofenac sodium ($\times 10^{-3}$ ppm) and with (DIC) being total diclofenac concentration (mMol); and FIG. 8 depicts energy minimized molecular models of possible modes of inclusion as indicated by proton magnetic resonance experiments described in Example 7.

DESCRIPTION OF EMBODIMENTS

Figure 4A:
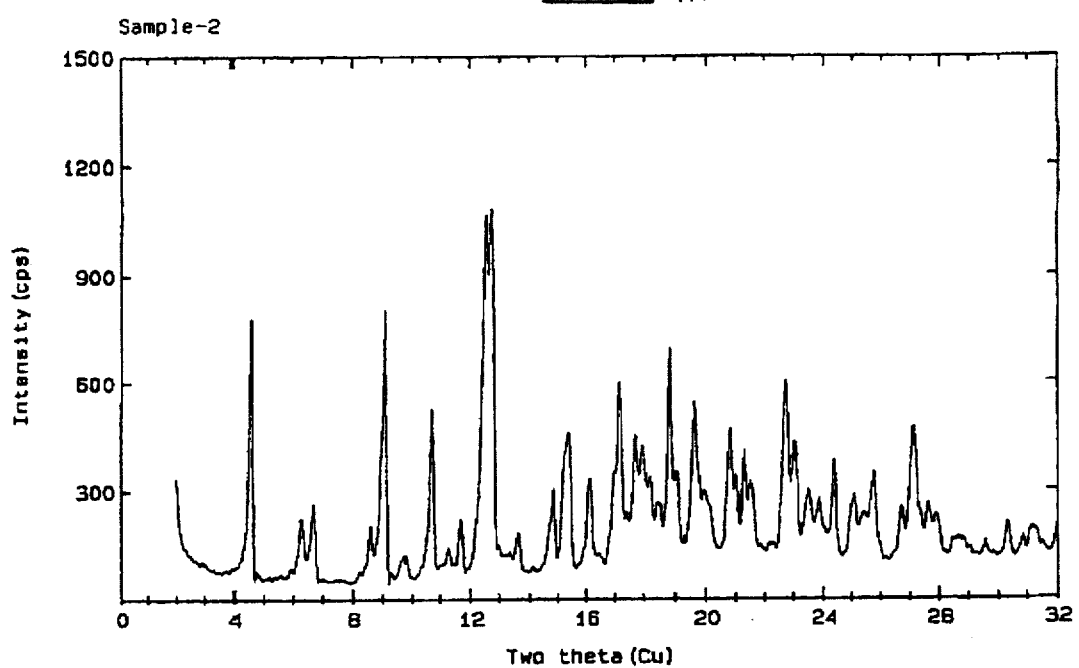
FIGS. 4A and 4B are X-ray powder diffraction patterns for Sample 1 (inclusion complex from Example 2) and Sample 2 (diclofenac sodium and beta-cyclodextrin as a stoichiometric physical mixture) directly measured over the 2-theta range 0–32 degrees on a powder diffraction X-ray goniometer using Cu-Kα radiation ($\lambda=1.5418$ Å)

The crux of the invention is that there is formed an inclusion compound or complex of diclofenac and an unsubstituted beta-cyclodextrin, with certain specific characteristics.

There are various processes for forming this inclusion compound or inclusion complex. A first way of forming the inclusion compound or complex involves the formation of a paste. A second way of forming the inclusion compound or complex involves the formation of a slurry. These two processes are set out in more detail below.

PASTE (1) The required amount of pre-screened diclofenac or a pharmaceutically acceptable salt thereof and the beta-cyclodextrin are mixed.

(2) A suitable amount of water, preferably deionised purified water, is added to the mixture of step (1) with vigorous mixing until a paste-like consistency is reached.

(3) The mixing or kneading is continued, with further addition of water if necessary to maintain the paste like consistency, for a suitable period of time to form the inclusion complex, preferably for a time of from 0.25 hours to 1 hour.

(4) The product of step (3) is dried.

Thereafter, the product may be screened.

SLURRY (1) The required amount of pre-screened diclofenac or a pharmaceutically acceptable salt thereof and the beta-cyclodextrin are mixed, optionally with microcrystalline cellulose in an amount of 5–15% m/m.

(2) A suitable amount of water, preferably deionized purified water, is added to the mixture of step (1) with vigorous mixing and with optional heating until a slurry is formed.

(3) The mixing is continued with further addition of water if necessary to maintain the slurry consistency for a suitable period of time to form the inclusion complex, preferably from 0.25 hours to 1 hour.

(4) Optionally, the slurry is passed through a colloid mill.

(5) The slurry is dried, preferably spray dried or spray granulated, to give the product.

Evidence for complexation is provided by solubility data, infrared spectrometry and X-ray powder diffraction.

Compared with solution processes of complexation (co-crystallization or precipitation, spray drying or freeze drying) the processes according to the invention provide the following advantages:

(i) satisfactory complexation within one hour as opposed to several hours, days or weeks (ii) reduced mounts of solvent (iii) high yield (iv) high solubility owing to favourable particle size distribution (v) suited for industrial application A third way of forming an inclusion compound or complex of diclofenac or a pharmaceutically acceptable salt thereof is set out below. This third process includes the steps of:

(1) dissolving a suitable amount of diclofenac or a pharmaceutically acceptable salt thereof and a suitable amount of an unsubstituted beta-cyclodextrin in water at an elevated temperature; and (2) cooling the solution and allowing the formation of the inclusion complex by evaporation of the water over a period of time. (The period of time may be from one hour up to and exceeding 1 day.)

The inclusion complex of the invention is an inclusion complex of diclofenac or a pharmaceutically acceptable salt thereof and an unsubstituted beta-cyclodextrin, with a molar ratio of diclofenac or a pharmaceutically acceptable salt thereof, calculated as diclofenac free acid, to unsubstituted beta-cyclodextrin, of 1:1, and preferably has solubility in deionized water of greater than 10 mg diclofenac per milliliter at 20° C. and pH5–7.

The inclusion complex preferably has a molecular composition of one molecule diclofenac as a pharmaceutically acceptable salt, e.g. diclofenac sodium or diclofenac potassium, one molecule of unsubstituted beta-cyclodextrin and from 5 to 11 water molecules inclusive.

Preferably, the complex has substantially the X-ray diffraction pattern of FIG. 3 or Sample 1 of FIG. 4.

The inclusion complex may be formulated in a pharmaceutical composition, for example a pharmaceutical composition suitable for oral administration. For example, the pharmaceutical composition may be presented in the form of a tablet, a capsule, or a powder, suitable for oral administration.

Various examples of the preparation and characterisation of inclusion complexes formed between β-cyclodextrin and a diclofenac salt, diclofenac sodium, will now be given.

EXAMPLE 1

The complex is prepared by mixing 56 mg of diclofenac sodium and 200 mg of β-cyclodextrin in 2 ml distilled water at 70° C. until dissolved completely. The solution is then cooled slowly to room temperature over approximately 12 hours and left to stand for a number of weeks whereupon the complex crystallizes as fine colourless needles with an hexagonal cross-section. It is important to note that the β-cyclodextrin was not dried prior to use and from thermogravimetric analysis contained approximately 10.75 water molecules per β-cyclodextrin molecule. The ratio of diclofenac sodium to β-cyclodextrin used is therefore 1:0.85 and weights may require adjustment depending on water content of raw materials. More rapid precipitation of the complex can be achieved if the concentration is increased approximately four times. However, this may require a smaller ratio of β-cyclodextrin to diclofenac sodium to avoid precipitation of β-cyclodextrin hydrate. The fine needles of the complex can easily be distinguished microscopically from crystals of β-cyclodextrin or diclofenac sodium which crystallize from water as colourless prisms and thin sheets (fast crystallization) respectively.

FIG. 1 shows details of the host-guest interactions which include both hydrogen bonding and hydrophobic interactions between the phenylacetate residue of the drug anion and β-CD. The phenyl ring is fully inserted in the β-CD cavity while one carboxylate oxygen atom, O(18), is hydrogen bonded to a primary hydroxy group of the same β-CD molecule [O(18) . . . O(6G6) 2.729(6) Å]. Consequently, this primary hydroxy adopts the +gauche form with the C(6)—O(6) bond directed towards the host cavity in contrast to the six remaining primary hydroxy groups which adopt the −gauche conformation, as usually observed. The orientation of the carboxylate group is determined by an intramolecular hydrogen bond N(3)—H(3) . . . O(19)[N . . . O]2.829(7) Å] which also occurs in the crystal structure of sodium diclofenac tetrahydrate. The bulky dichlorophenyl moiety, whose minimum dimension is close to the maximum effective diameter of the apolar host cavity (7.8 Å), protrudes from the primary face of the host and is sandwiched between the β-CD molecule shown in FIG. 1 and one directly above, related by a crystallographic screw hexad. The $Na^+$ ion is situated at the periphery of the β-CD molecule and is approximately octahedrally co-ordinated by oxygen atoms of three water molecules [O(1W), O(6W), O(9W)], a primary hydroxy group of β-CD [O(6G6)], and two secondary hydroxy groups of a symmetry-related host molecule [O(2G4$^I$), O(3G4$^I$),1=I+y,1−x+y,−⅙+z). The $Na^+$ . . . O distances are in the range 2.269(6)–2.611(6) Å.

The complex units stack in a regular head-to-tail mode via a $6_1$-axis which passes through the β-CD cavity and is nearly normal to the plane of the β-CD molecule. As shown in FIG. 2, this results in an endless helical host channel with a pitch of 51 Å. An important interaction contributing to the head-to-tail stacking is a strong hydrogen bond between carboxylate oxygen atom O(19) and the secondary hydroxy group O(3G6$^{II}$) of a $6_1$-related β-CD molecule (II=y,−x+y,−⅙+z) with O . . . O 2.565(6) Å and O—H . . . O 171(2)°. Other stabilizing interactions between the primary face of the β-CD molecule shown in FIG. 1 and the secondary face of a $6_1$-related host molecule are O(6G7)—H . . . O(3G$^{II}$) with O . . . O 2.639(7) Å, O—H . . . O 175(3)°, O(6G4) . . . H—O (2G6$^{II}$) with O . . . O 2.690(8) Å, O—H . . . O 146(11)°, and hydrogen bonds mediated by bridging water molecules, O(6G2)—H . . . O (5W$^{III}$)—H . . . O (2G3$^{II}$) (III=−1+x, y, z) and O(18) . . . H—O(1W)—H . . . O(2G7$^{II}$).

The conformation of the β-CD molecule in this complex is distorted to a greater extent than is usually observed. The heptagon composed of O(4) atoms is irregular with side lengths in the range 4.238(7)–4.496(5) Å and the angles subtended at the O(4) atoms are in the range 120.1°–131.6°. This distortion is partly due to the dichlorophenyl residue which rests on the secondary face of the host. The tilt angles for glucose residues G1–G7 are 5.5°, 4.2°, 13.5°, 28.7°, 7.0°, 11.8° and 31.7°. The largest values, for G4 and G7, can be attributed to an intermolecular hydrogen bond O(2G4)—H . . . O(3G7$^{1V}$) (1V=x.−1+y,z). Despite these distortions, the distances O(3Gn) . . . O[2G(n+1)] are in a relatively narrow range of 2.716(6) to 3.022(7) Å and the usual intramolecular hydrogen bonds which impart 'roundness' to β-CD appear to be largely maintained.

Columns of complex molecules, one of which is shown in FIG. 2, pack in a hexagonal array and are held together by a complex network of hydrogen bonds involving β-CD hydroxyl groups and water molecules. The complex thus crystallizes in infinite layers (plane group p6) parallel to the (001) planes, complex molecules in each successive layer being rotated by 60° about the c-axis from those in the layer above.

The thermal decomposition of the complex has been studied by thermogravimetry(TG) and differential scanning calorimetry(DSC).

Thermogravimetric analysis shows a 12.02 weight percent loss between 25° C. and 150° C., which corresponds to 11 water molecules of crystallization.

The water molecules were exceptionally well-behaved at the low temperature of the X-ray analysis, yielding final $U_{eq}$ values in the range 0.03–0.08 Å$^2$ and showing no signs of disorder. The TG trace indicated that dehydration occurs in at least four steps, each of which is accompanied by a corresponding endotherm in the DSC trace. It is possible to rationalize these observations on the basis of the different environments of the water molecules in the crystal, those involved in weak hydrogen bonds being released first and those coordinated to Na$^+$ or engaging in multiple hydrogen bonds desorbing during the later phases of mass loss. TG, DSC and thermomicroscopy indicate that on further heating, the complex does not melt but begins to decompose at approximately 473 K.

EXAMPLE 2

Diclofenac sodium (6.6 g) and beta-cyclodextrin (23.4 g) are screened (30 mesh) and ramble mixed. The mixture is transferred to a mortar. Deionized water (10–15 ml) is gradually added with vigorous mixing to produce a uniform paste. Vigorous mixing is continued for 0.5 hours ensuring a uniform paste-like consistency throughout the operation. The mixture is oven dried at 40° C. The dried mass is crushed and passed through 30 mesh screen. The powder is homogenized in a powder mixer for 10 minutes. The product contains 21% m/m diclofenac sodium as determined by HPLC. The water content of the product is between 9 and 11% m/m as determined by Karl Fisher titration. The molecular composition of the product thus corresponds to 1 molecule diclofenac sodium, 1 molecule beta cyclodextrin and between 7 and 10 water molecules. The particle size of the product corresponds to 90% less than 30 microns as measured under a light microscope. The morphology of the complex resembles very fine fractured crystalline particles.

EXAMPLE 3

Diclofenac sodium (841 g), beta cyclodextrin (3000 g) and microcrystalline cellulose (580 g) are blended in a ramble mixer for 10 minutes and transferred to a mixing vessel. Purified deionized water (10.5 liters) is added and the mixture is vigorously stirred for 0.5 hr to produce a uniform slurry. The slurry is treated with a colloid mill and immediately spray dried under the following conditions using rotating disc atomization: inlet temperature 150° C.; outlet temperature 60° C.; feed rate 5 liters per hour. The product (3927 g) is obtained in 89% yield and contains 20% m/m diclofenac sodium as determined by HPLC. The water content of the product is between 7 and 11% m/m as determined by Karl Fisher titration. The molecular composition of the product thus corresponds to 1 molecule diclofenac sodium, 1 molecule beta cyclodextrin and between 5 and 10 water molecules in addition to microcrystalline cellulose. The particle size of the product corresponds to 90% less than 50 microns as measured under a light microscope. The morphology of the complex resembles very fine spheroidal amorphous particles.

EXAMPLE 4

The complex (500 mg) prepared according to Example 2 is added to 2 ml deionized water at room temperature in a screw cap vial. The vial is sealed and placed in a laboratory shaker. The mixture is allowed to shake for 5 minutes and then equilibrated for 24 hours. The supernatant is filtered through a 0.22 micron filter and analyzed for diclofenac concentration by HPLC. The equilibrium water solubility of the complex corresponds to 38 mg/ml diclofenac sodium. The equilibrium solubility of diclofenac sodium in the absence of beta cyclodextrin under identical conditions is 5 mg/ml.

EXAMPLE 5

Figure 4B:
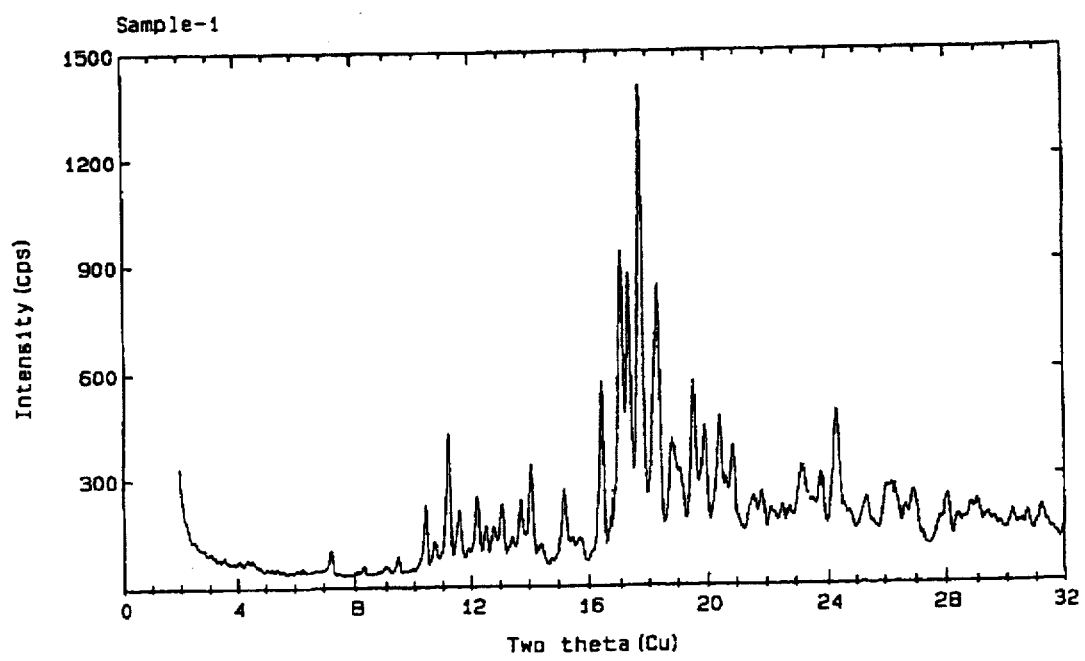

A sample (Sample 1) of the inclusion complex obtained in Example 2 is analyzed by X-ray powder diffraction. A stoichiometric physical mixture is prepared by tumble mixing 0.66 g diclofenac sodium with 2.34 g beta-cyclodextrin. A sample of the physical mixture (Sample 2) is analyzed by X-ray powder diffraction under identical conditions to Sample 1. The peak positions in Sample 2 correspond with the sum of individual diffraction patterns for diclofenac sodium and beta-cyclodextrin. Sample 1 shows entirely different peak positions when compared with Sample 2 and bears significant resemblance to the pattern shown in FIG. 3. The X-ray powder diffraction pattern of Sample 1 is therefore characteristic of a crystalline form distinct from either diclofenac sodium or beta-cyclodextrin and may be taken as direct evidence of inclusion complexation. The X-ray powder diffraction patterns of Sample 1 and Sample 2 are shown in FIGS. 4A and 4B.

EXAMPLE 6

Figure 5:
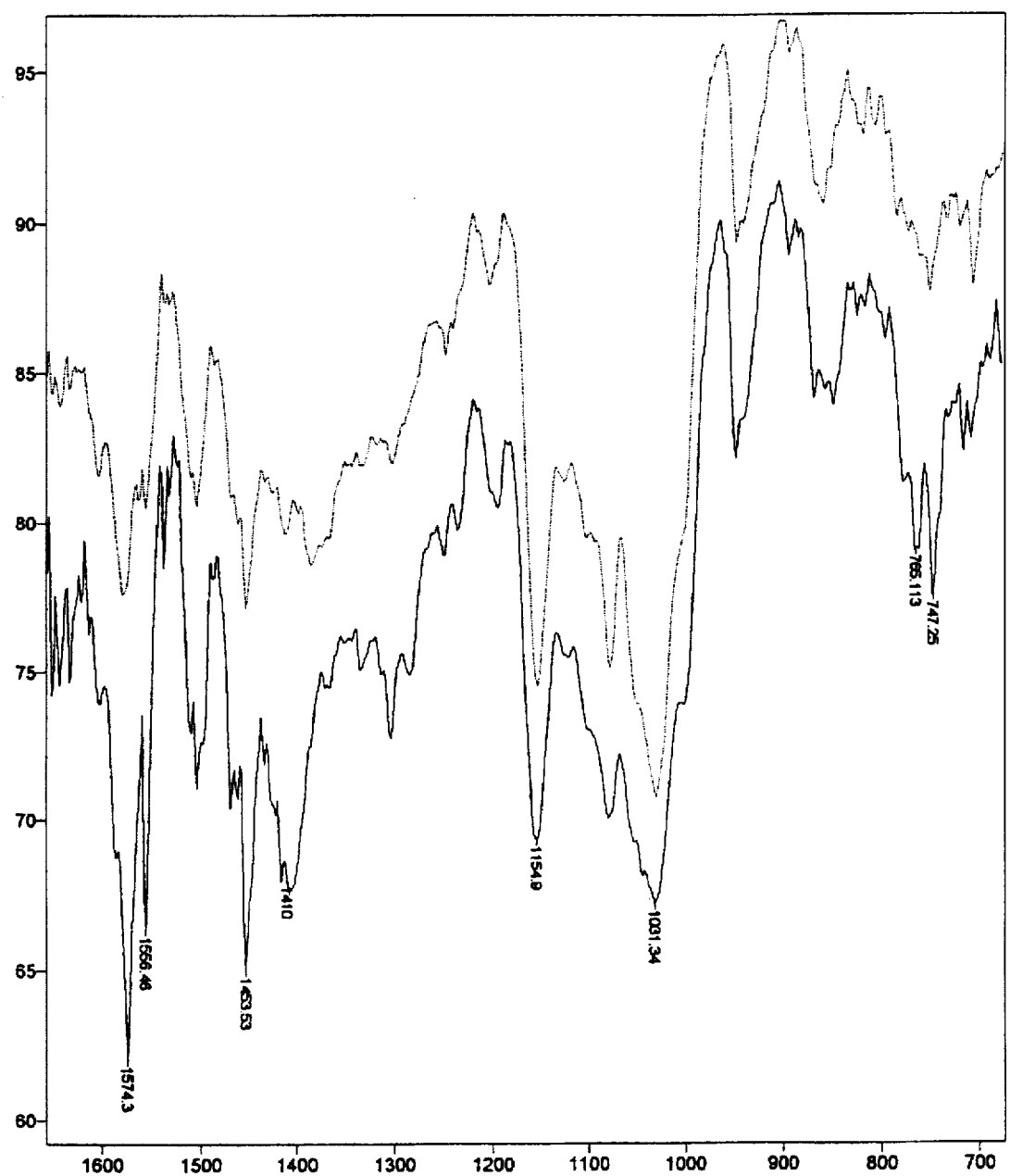
FIG. 5 is a portion of the infrared spectra of diclofenac sodium and beta-cyclodextrin as stoichiometric physical mixture (solid line) and an inclusion complex (dotted line) as described in Example 6. Important bands are annotated with wave numbers ($cm^{-1}$)

A stoichiometric physical mixture is prepared by tumble mixing 0.66 g diclofenac sodium with 2.34 g beta-cyclodextrin. A sample of the mixture (3 mg) is triturated with 300 mg potassium bromide (KBr) in an agate mortar. A sample of the complex obtained from Example 2 (3 mg) is triturated with 300 mg potassium bromide (KBr) in an agate mortar. The sample cup of a diffuse reflectance infrared accessory is filled with KBr and the sample analyzed as background by fourier transform infrared spectrometry on a Perkin-Elmer Paragon 1000 instrument using 16 scans with a resolution of 4 cm$^{-1}$. The KBr/physical mixture and KBr/complex samples are run under identical conditions with subtraction of the background and are shown in FIG. 5. Relative to the physical mixture, the complex shows similar absorption intensity for bands associated with the cyclodextrin (for example stretch frequencies of glycosidic C—O groups and C—C groups at 1155 cm$^{-1}$ and 1031 cm$^{-1}$ respectively [Spectroscopic studies on β-Cyclodextrin, Egyed, O. Vibrational Spectroscopy 1990,1,225–227]). Characteristic reduction in infrared absorption of diclofenac is observed in the complex relative to the physical mixture, particularly in the regions corresponding to intense carboxylate stretch frequencies (1550–1600 cm$^{-1}$) and aromatic stretch frequencies (1400–1550 and 680–800 cm$^{-1}$) as shown in FIG. 1. When measured relative to the strong beta-cyclodextrin C—O and C—C absorption bands at 1155 and 1031 cm$^{-1}$ respectively, the reduction in intensity of the diclofenac bands at 1574, 1556, 1453, 1410, 765 and 747 is between 40 and 60%. The reduced intensity is due to vibrational restrictions imposed on the guest molecule in the cyclodextrin cavity and may be taken as direct evidence of inclusion complexation.

EXAMPLE 7

The reaction between diclofenac sodium and beta-cyclodextrin in water may be demonstrated by proton nuclear magnetic resonance (NMR) spectrometry. Proton magnetic resonance experiments were performed on a Bruker $AMX_R$ 500 spectrometer with probe temperature at 303K. Solutions of diclofenac sodium (DIC) and beta-cyclodextrin (BCD) were prepared in $D_2O$ and mixed in varying proportions to obtain continuous variation plots (Job plots) from which complex stoichiometry may be interpolated. The total concentration [DIC]+[BCD] was kept constant (10 mM) and the ratio (r) was varied from 0.1 to 0.9, where r=[DIC]÷[DIC]+[BCD]. Chemical shifts (δ) were measured relative to external tetramethylsilane. Two-dimensional nuclear Overhauser enhancement (NOE) spectra were recorded in the rotating frame (ROESY) for a solution of DIC/BCD with r=0.4. A spin locking time of 150 ms was used.

Figure 6:
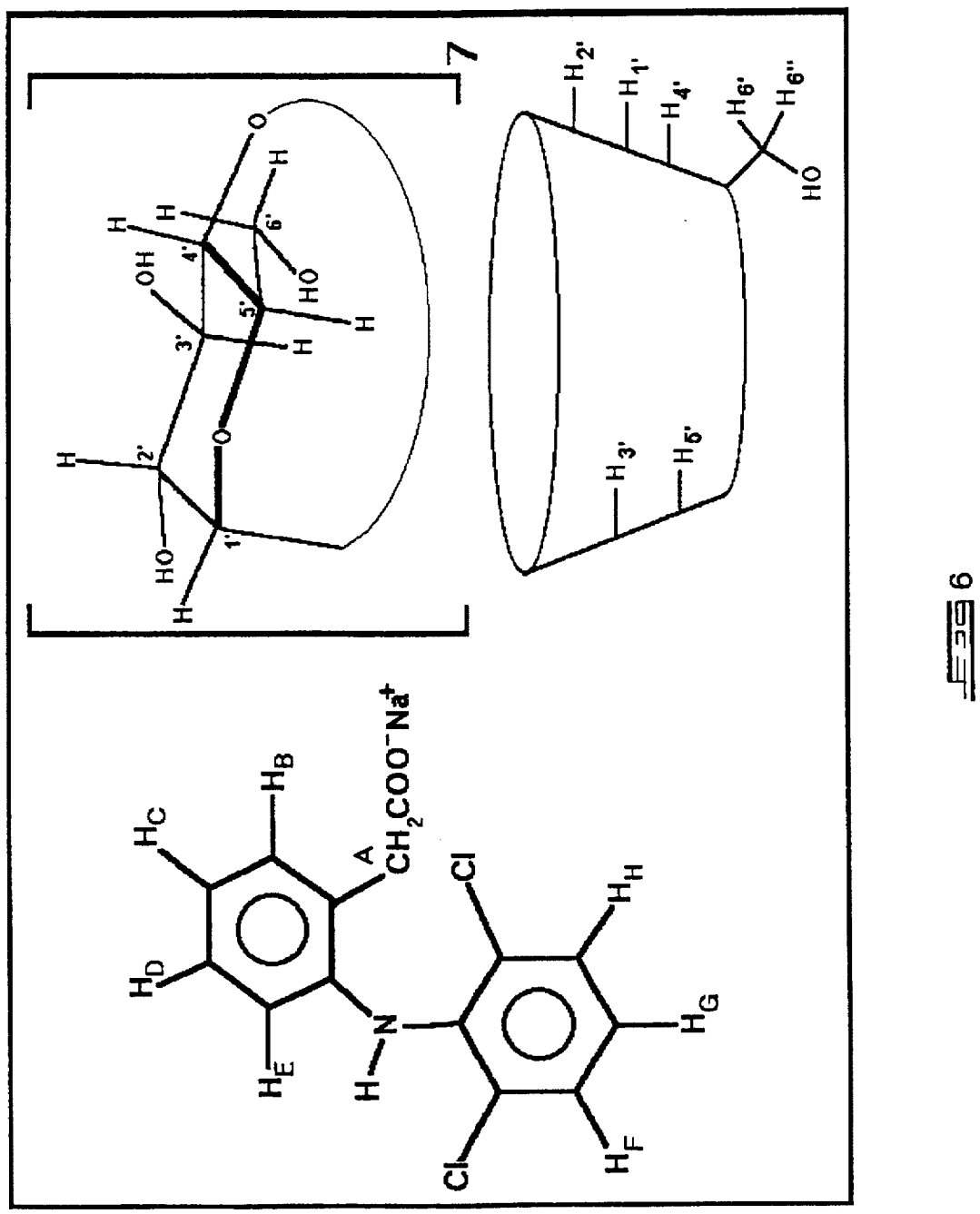
FIG. 6 depicts the structure and proton notation of diclofenac sodium and beta-cyclodextrin as used in the description of Example 7.

Molecular modeling was performed using Hyperchem™ software. Molecular mechanics calculations involving rigid body docking and energy minimizations were performed using the MM+ force field. Initial structures of BCD and DIC were based on X-ray data. Calculations were performed on the two possible 1:1 isomeric complexes as well as on the 1:2 DIC/BCD complex. The structure and notation of DIG and BCD are shown in FIG. 6.

Figure 7B:
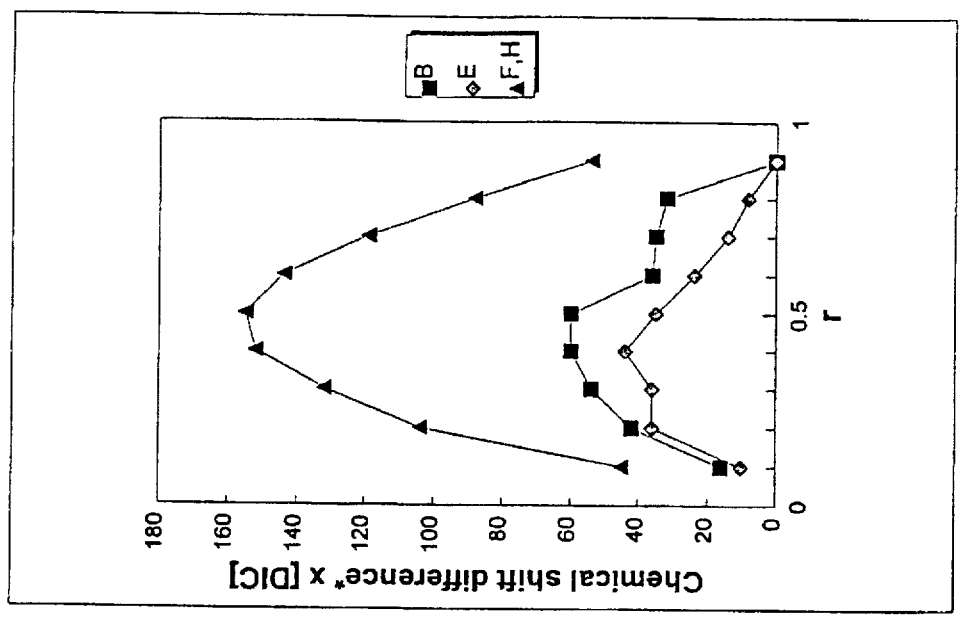
FIGS. 7A and 7B are continuous variation (Job) plots obtained from proton magnetic resonance spectra of a solution of diclofenac sodium and beta-cyclodextrin in deuterated water as described in Example 7.
Figure 7A:
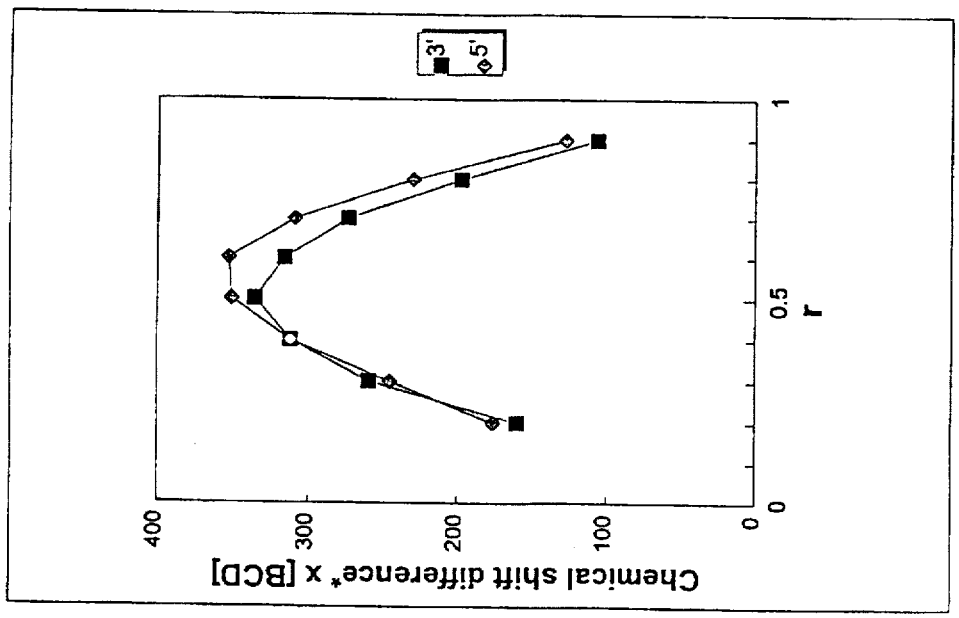

Plots of the observed Δδ•[BCD] or Δδ•[DIC] as a function of r leads to Job plots given in FIG. 7. The internally oriented 3' and 5' BCD protons as well as the F,H chlorophenyl protons give large shifts and symmetrical curves with a maximum at r=0.5 indicating a 1:1 stoichiometry. In the case of the phenylacetate B,E protons, small shifts were observed giving rise to unsymmetrical curves with the maximum at r apparently less than 0.5. This result suggests the possible formation of a 1:2 DIC/BCD complex.

From the 2D ROESY spectrum, cross peaks were observed between F,H and 3',5' and between E and 3' protons indicating through space couplings between spatially close (<4 Angstrom) protons of the cyclodextrin and diclofenac respectively. Together the NMR results indicate preferential complexation of the more hydrophobic dichlorophenyl ring with a smaller proportion of structures corresponding to inclusion of the phenylacetate ring. These findings are schematically depicted as energy minimized molecular models shown in FIG. 8.

Based on the high resolution nuclear magnetic resonance studies of diclofenac sodium and beta cyclodextrin there is direct evidence to support different modes of inclusion in aqueous solutions involving both dichlorophenyl and phenylacetate moieties in diclofenac. Therefore, during the paste and slurry complexation processes according to the invention it is likely that different types of inclusion compound are produced to varying extents.

EXAMPLE 8

The inclusion complex of beta-cyclodextrin-diclofenac sodium obtained according to the invention may be formulated into tablets with the following unit composition:

| | |
|---|---|
| Diclofenac sodium-beta cyclodextrin complex (equivalent to 50 mg diclofenac sodium) | 220 mg |
| Starch | 100 mg |
| Ac-di-sol | 20 mg |
| Magnesium stearate | 4 mg |
| | 344 mg |

The Ac-di-sol, microcrystalline cellulose and starch are premixed in a blender. The diclofenac sodium-beta cyclodextrin complex is added to the mixture and blended. The magnesium stearate is screened in and blended. The mixture is compressed into tablets.

We claim:

1. A crystalline inclusion complex of diclofenac or a pharmaceutically acceptable salt thereof and an unsubstituted beta-cyclodextrin which has a molar ratio of diclofenac or a pharmaceutically acceptable salt thereof to the unsubstituted beta-cyclodextrin of 1:1 and a molar ratio of diclofenac or a pharmaceutically acceptable salt thereof to the unsubstituted beta-cyclodextrin to water of 1:1:5 to 1:1:11 produced by the steps of:
   (a) mixing the diclofenac or the pharmaceutically acceptable salt thereof and the beta-cyclodextrin;
   (b) adding a suitable amount of water to the mixture of step (a) with vigorous mixing until a paste or a slurry is formed;
   (c) continuing the mixing with further addition of water if necessary to maintain the paste or slurry consistency, for a suitable period of time to form the inclusion complex; and
   (d) drying the product of step (c) to form the crystalline inclusion complex as product.

2. An inclusion complex according to claim 1 which has a solubility in deionized water of greater than 10 mg diclofenac per milliliter at 20° C. and a pH of 5–7.

3. An inclusion complex according to claim 1 wherein the diclofenac is present in the complex as diclofenac sodium.

4. An inclusion complex according to claim 1 wherein the diclofenac is present in the complex as diclofenac potassium.

5. An inclusion complex according to claim 3 which has substantially the X-ray powder diffraction pattern of FIG. 3.

6. An inclusion complex according to claim 3 which has the formula (diclofenac sodium).(beta-cyclodextrin).$11H_2O$.

7. A process for preparing a crystalline inclusion complex of diclofenac or a pharmaceutically acceptable salt thereof and an unsubstituted beta-cyclodextrin in a 1:1 molar ratio which includes the steps of:
   (a) mixing the diclofenac or the pharmaceutically acceptable salt thereof and the beta-cyclodextrin;
   (b) adding a suitable amount of water to the mixture of step (a) with vigorous mixing until a paste or a slurry is formed;
   (c) continuing the mixing with further addition of water if necessary to maintain the paste or the slurry consistency, for a suitable period of time to form the inclusion complex; and
   (d) drying the product of step (c).

8. A crystalline inclusion complex according to claim 1 wherein in step (c) the mixing is continued for a period of time from 0.25 hours to one hour.

9. A pharmaceutical composition which comprises as active ingredient a crystalline inclusion complex of diclofenac or a pharmaceutically acceptable salt thereof according to claim 1.

* * * * *